(12) United States Patent
Bradamante et al.

(10) Patent No.: US 7,695,957 B2
(45) Date of Patent: Apr. 13, 2010

(54) BIOREACTOR, IN PARTICULAR FOR NMR SPECTROSCOPY

(76) Inventors: Silvia Bradamante, Via Tarvisio, 19, 20125 Milano (IT); Livia Barenghi, Via Compari, 19, 27100 Pavia (IT); Alessandro Villa, Largo Augusto, 8, 20122 Milano (IT)

( * ) Notice: Subject to any disclaimer, the term of this patent is extended or adjusted under 35 U.S.C. 154(b) by 1188 days.

(21) Appl. No.: 11/188,152

(22) Filed: Jul. 22, 2005

(65) Prior Publication Data

US 2007/0020751 A1  Jan. 25, 2007

(51) Int. Cl.
- *C12M 1/00* (2006.01)
- *C12M 3/00* (2006.01)
- *C12N 5/00* (2006.01)
- *G01V 3/00* (2006.01)

(52) U.S. Cl. .............. 435/293.2; 435/289.1; 435/293.1; 435/383; 324/307; 324/300; 324/309; 324/318

(58) Field of Classification Search .............. 435/289.1, 435/293.1, 293.2, 383; 324/300, 307, 309, 324/318
See application file for complete search history.

(56) References Cited

U.S. PATENT DOCUMENTS

| | | | |
|---|---|---|---|
| 5,002,890 A * | 3/1991 | Morrison ................. | 435/297.3 |
| 5,313,162 A | 5/1994 | De Graaf et al. | |
| 5,469,061 A | 11/1995 | Linehan et al. | |
| 5,556,765 A * | 9/1996 | Dedolph ....................... | 435/41 |
| 5,846,817 A * | 12/1998 | Mausli ..................... | 435/293.1 |
| 5,989,913 A | 11/1999 | Anderson et al. | |

FOREIGN PATENT DOCUMENTS

DE  4213058 A1  10/1992
FR  2816713 A1  5/2002

OTHER PUBLICATIONS

Chopra et al., Three-Dimensional Endothelial-Tumor Epithelial Cell Interactions in Human Cervical Cancers, 1997, In Vitro Cell. Dev. Biol.-Animal, 33(6), p. 432-42.
Bradamante et al., Intracellular Magnesium Homeostasis is Inovlved in the Functional Recovery of Preconditioned Rat Heart, Biochemical and Biophysical Research Communications, 1993, vol. 196, p. 872-876.

(Continued)

*Primary Examiner*—William H Beisner
*Assistant Examiner*—Nathan A Bowers
(74) *Attorney, Agent, or Firm*—James C. Eaves, Jr.; Greenebaum Doll & McDonald PLLC; Brian W. Chellgren

(57) ABSTRACT

A description is given of a bioreactor (1), in particular for NMR spectroscopy, comprising a container (7) capable of containing a cell culture, a first inlet line (6) for the inward flow of a culture medium to the inside of the container and a second outlet line (9, 10) for the outward flow of the culture medium from the container (7). The first line (6), an inlet line, is connected to a spiral-shaped device (12) which has a form such that when the medium is made to flow inside the first line (6) and made to flow out of the second line (9; 10), hydrostatic thrust and hydrodynamic forces produce with respect to the cells a condition of simulated reduced gravity inside the container (7).

9 Claims, 2 Drawing Sheets

OTHER PUBLICATIONS

Bradamante et al., NMR Evaluation of Changes in Myocardial High Energy Metabolism Produced by Repeated Short Periods of Ischemia, Biochimica et Biophysica Acta, 1995, v. 1243, p. 1-8.

Carelli et al., Cysteine and Glutathione Secretion in Response to Protein Disulfide Bond Formation in the ER, Science, 1997, vol. 277, p. 1681-1684.

Carlsson et al., Modulation of Human Endothelial Cell Behaviour in Simulated Microgravity, Universita di Milano, Milano, Italy, p. 281-282.

Liu et al., Medium Optimization for Glutathione Production by *Saccharomyces cerevisiae*, Process Biochemistry, 1999, v. 34, p. 17-23.

Muhitch et al., Characterization of Aggregation and Protein Expression of Bovine Corneal Endothelial Cells as Microcarrier Cultures in a Rotating-Wall Vessel, Cytotechnology, 2000, vol. 32, p. 253-263.

Saarinen et al., Monitoring and Controlling the Dissolved Oxygen (DO) Concentration within the High Aspect Ratio Vessel (HARV), Biotechnol. Prog. 2003, 19, p. 1335-1341.

Udeh et al., Abstract of "High-Glutathione Containing Yeast *Saccharomyces cerevisiae*: Optimization of Production", Acta Microbiologica Polonica, 1997, v. 46(1).

Wei et al., Effect of surfactants on Extracellular Accumulation of Glutathione by *Saccharomyces cerevisiae*, Process Biochemistry, 38, 2003, p. 1133-1138.

Wu et al., Glutathione Metabolism and Its Implications for Health, Recent Advances in Nutritional Sciences, 2004 American Society for Nutritional Sciences, 2004, p. 489-492.

* cited by examiner

BIOREACTOR, IN PARTICULAR FOR NMR SPECTROSCOPY

The present invention relates to a bioreactor, in particular for NMR spectroscopy, according to the preamble to the main claim 1. A further subject of the invention is a method for increasing cell culture by means of said bioreactor and the intracellular and extracellular production of metabolites.

Within this field of reference technology, there is a known requirement to produce bioreactors in which the shear stress to which the cell cultures are subjected is sufficiently reduced so as to allow cell vitality even at the high densities required in many types of biotechnology production. For the same purpose, oxygenation and the availability of nutrients within the culture medium must be improved to obtain high-density cell cultures (animal, vegetable, yeasts etc.).

For this reason, bioreactors connected to perfusion systems have been designed, though these offer only partial solutions to the problems connected with cell stress due to mechanical agitation or to fluid and/or gas movements, often highly vigorous, to maintain adequate oxygenation which, above all in the case of mammalian cell cultures, are the cause of substantial damage.

Recent studies have indicated that simulated microgravity conditions can reduce shear stress. In fact, it has been observed that cell cultures growing in bioreactors using a device known as a Rotating Wall Vessel (RWV), the subject of U.S. Pat. No. 5,989,913, operating in simulated microgravity, are subjected to low turbulence and shear stress. In these conditions, there are reports of better proliferation and differentiation of some cell cultures (in particular mammalian cells), increased proliferation of micro-organisms and greater productivity of some metabolites (such as antibiotics and polyesters).

In addition, a further requirement in this field is the ability to carry out constant monitoring of cell vitality and productivity throughout the relevant process, which may be of long duration (numbered in days or weeks), a requirement which is particularly important in the biotechnology processes for the production of tissues, proteins, hormones, antibodies, drugs, food additives etc. In this context, nuclear magnetic resonance (NMR) spectroscopy is considered the technique of choice for prolonged, non-invasive and non-destructive monitoring of intracellular and extracellular production of some metabolites, and for the study of the various metabolic routes used for the production of primary and secondary metabolites.

However, to use NMR spectroscopy in vivo it has to be possible to reproduce in the containers suitable for insertion into an NMR spectrometer (known as NMR tubes) the controlled conditions of cell growth in the medium, which cannot be achieved by using RWV devices. Moreover, NMR spectroscopy analysis of the metabolism in vivo requires high cell density, increasing the problems connected with control of the chemical-physical parameters of the medium in which the cells are present and of the transport of oxygen.

The problem addressed by the present invention is that of making available a bioreactor, in particular for NMR spectroscopy designed to eliminate all the disadvantages noted with reference to the known technology cited.

Furthermore, a purpose of the invention is to produce a bioreactor which retains the main advantages of bioreactors operating in simulated microgravity but which at the same time is suitable for analysis of the NMR type to monitor the metabolism of the cell cultures non-invasively and in real time.

This problem is solved and these purposes are achieved by the invention by using a bioreactor and a method of cell culture, in particular for NMR spectroscopy, according to the invention.

The characteristics and advantages of the invention will become clear from the following detailed description of a preferred example of embodiment illustrated purely by way of non-limiting example with reference to the appended drawings in which.

Figure 1:
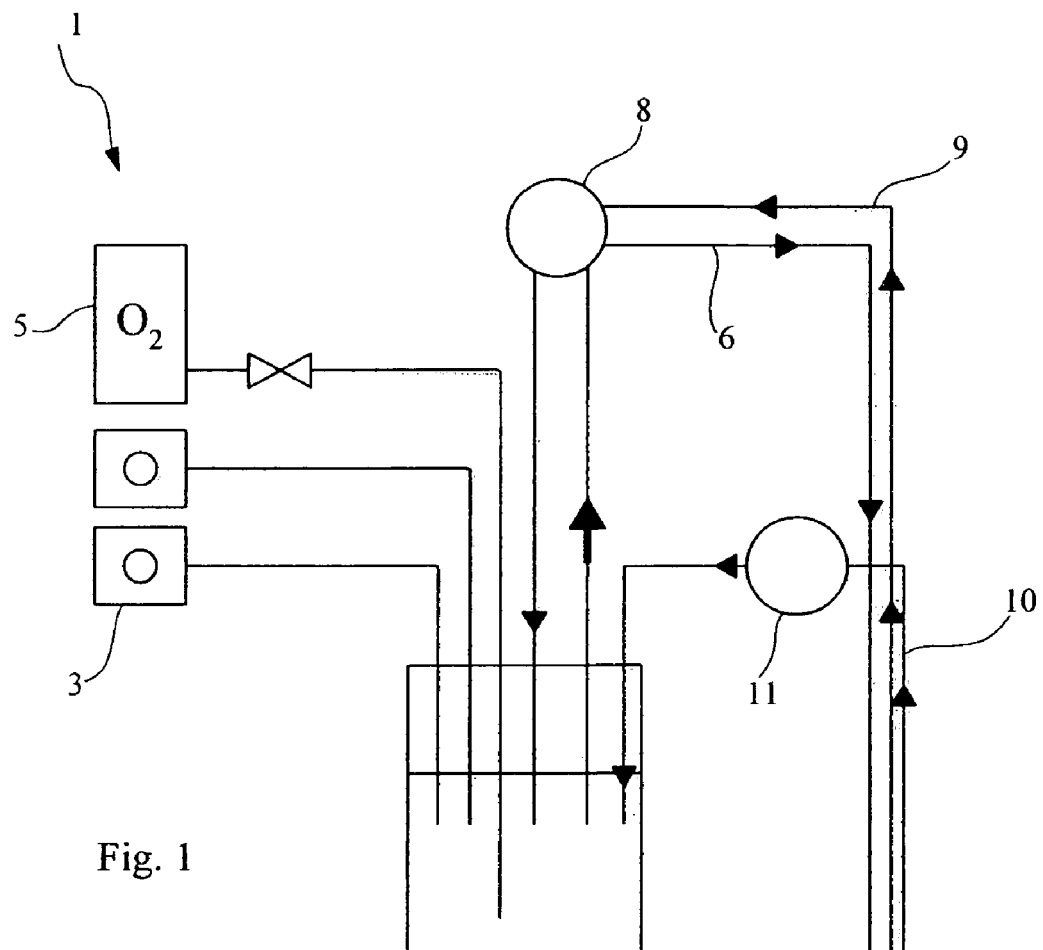
FIG. 1 is a schematic view of a bioreactor produced according to the invention.
Figure 2:
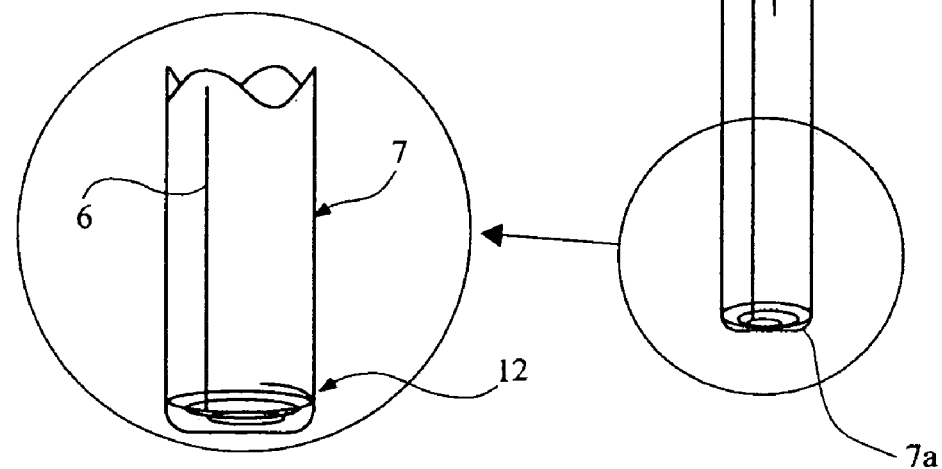
FIG. 2 is a detail at an enlarged scale of the bioreactor in FIG. 1.

Referring initially to FIG. 1, the number 1 indicates as a whole a bioreactor, in particular for NMR spectroscopy, produced according to the invention.

Of course, although in the description which follows NMR spectroscopy is indicated as the preferred application of the bioreactor 1 in question, the bioreactor disclosed by the invention can be used both with a plurality of systems for recording and monitoring culture cells, being particularly suitable for photometry, fluorimetry, in vivo imaging and confocal microscopy, and, in the absence of monitoring, as a separate bioreactor.

In fact, as will become clearer in what follows, the bioreactor 1 is an alternative to RWV bioreactors since similar simulated microgravity conditions are obtained, and in addition it provides improved oxygenation and compatibility with equipment for recording cell vitality in vivo, such as NMR.

The bioreactor 1 comprises a thermostatically controlled reservoir 2, including a plurality of necks, a reservoir in which a medium is kept at the temperature necessary for the specific culture undergoing analysis. The reservoir 2 also comprises a system 5, variable where appropriate, for delivering the gases necessary for cell survival or for the production of substances from microorganisms, such as oxygen and carbon dioxide, for example.

In contact with the medium inside the reservoir 2, there is also arranged an electrode of a pH-meter 3 to monitor the pH of the medium and a sensor 4 of the oxygen dissolved within the medium. Provision is also made for a temperature monitoring-system, in the case in question integrated with the oxygen sensor 4.

Running from the reservoir 2 is a first line 6, in particular a capillary tube leading to a cylindrical container 7, of glass or plastics material, in such a way that the culture medium is able to circulate from the reservoir 2 through the line 6 to the container 7.

Also extending to the reservoir 2 are a second and a third line 9, 10, by means of which the medium is returned to the reservoir 2 from the container 7. Circulation of the medium from the reservoir 2 to the container 7 and its return to the reservoir 2 are controlled by peristaltic pumps 8, 11, which are also used to keep the quantity of medium inside the container 7 substantially constant.

The two lines 9, 10 coming out from the container 7 are provided for safety reasons, in particular because, when the container 7 is placed inside the NMR spectrometer, if accidental blockage of one of the two lines 9, 10 should occur, the second of these prevents escape of the medium inside the spectrometer itself, which would involve a time-consuming and costly operation to clean the spectrometer.

Additionally, if required for the type of cells examined or the type of analysis desired, a device (not shown) may be added to the bioreactor 1 for continuous or discrete delivery into the reservoir 2, into the container 7 or along any one of the lines 6, 9, 10 of compounds to control the metabolism, having a pharmacological action or controlling growth and apoptosis.

In the case where an investigation of the NMR type is not carried out, the cylindrical container 7 is jacketed in so as to preserve the temperature of the medium set in the reservoir 2; on the other hand, in the case of NMR spectroscopy, the temperature of the container 7 is controlled by the NMR instrumentation.

According to a principal characteristic of the invention, the first line 6 for the outlet of the medium from the reservoir 2, entering the inside of the container 7, and in particular at the bottom 7a of the latter, terminates in a spiral capillary device 12, that is a portion of capillary tube having a spiral form, the function of which will be described in more detail in what follows.

If the experiment to be carried out requires cell growth at a particularly high concentration, of the order of $10\text{-}25 \times 10^6$ cells/ml, useful for example for the production of recombinant biomolecules, the bioreactor 1 further comprises a filtration system, in particular a membrane system, for retention of the cells in culture, together with their substrates (analysed in more detail below), if any, inside the container 7.

The cells present in the bioreactor 1, or more precisely in the container 7, are then analysed by means of recording and monitoring equipment, such as an NMR spectrometer, conventional in itself.

In use, the various reservoirs, containers, inward flow lines for the medium and sensors, where necessary, are sterilized and fitted under sterile conditions before the desired experiments are carried out.

The desired temperature of the medium is then selected, generally variable between 10° C. and 40° C. according to the type of culture to be analysed, a temperature which is brought about by means of a suitable thermostatically controlled system (not shown in the drawings).

The culture medium is therefore prepared, its composition clearly depending on the type of cell culture analyzed. Moreover, the medium may be supplemented or conditioned, may be devoid of serum or proteins, recycled or with tracers or thickeners added in order to obtain optimum growth of the desired cells.

As indicated above, supplements may where appropriate be added to the medium to increase cell growth, gene expression and the production of primary and secondary metabolites. Examples of supplements are mineral salts, amino acids, glucides, lipids, proteins, growth factors, vitamins etc. A medium of this kind is poured into the reservoir 2, inside which it is oxygenated by means of the oxygen delivery system until the desired percentage of dissolved oxygen is reached, monitored by means of the sensor 4. Similarly, the pH of the medium is monitored by means of the pH-meter 3.

Provision is also made, in order to monitor the primary and secondary metabolism of the cells (which, as stated above, may be monitored in the bioreactor by means of a plurality of items of equipment, not only NMR spectroscopy) for introducing into the medium suitable tracers such as isotopes, chromophores, pH indicators or ions and contrast means depending on the type of investigation selected.

The cells examined may be of various types, whether animal or vegetable, micro-organisms or yeasts and may be free in the medium or anchored to substrates or encapsulated. The anchorage substrates may have a different density, such as for example microcarrier beads, non-porous or porous, constituted from polymers or mineral matrices; again, the encapsulation substrates may be of the microcarrier type, sponges, of a permanent or biodegradable type, or produced from polyurethane and polypeptide biomaterials.

These culture cells are positioned inside the container 7. The medium described above is prepared in the reservoir 2, and made to circulate by means of the peristaltic pumps 8, 11 inside the first line 6 until the spiral device 12 is reached, from which it flows out in such a manner that it is in contact with the cells and where applicable their substrates, then returning to the reservoir 2 via the lines 9 and/or 10. The flow of the medium, the course of which is detailed below, is such that the substrates and the cells can always remain inside the container 7.

The density of the medium may if necessary be varied in such a way that the substrates of the cells are less packed. The substances used to increase the above-mentioned density may be proteins, serum, deuterated water, methyl cellulose, pluronicotm™ F68, polyvinyl alcohols, polyvinyl pirrolidones, dextrans, polymers. For the same purpose, the velocity of the medium from and through the container 7 is regulated.

The flow of the medium, because of the particular form of the capillary tube 12 in the area in which the cells are present, creates an effect of absence of weight (simulated reduced gravity) or a mean absence of weight (reduced gravity) in the cell growth environment. These reduced gravity conditions are obtained by a suitable combination of the forces acting on the system in culture: hydrostatic thrust and hydrodynamic forces produced by introduction of the medium at a certain velocity and pressure, so that a flow-lift effect is obtained. Associated with this method of "reduction" of gravity is a decrease in shear stress, an effect obtained as set out further on.

The same combination of hydrostatic and hydrodynamic forces is responsible for the low shear stress to which the cells are subjected. The relative velocity (Vrel) of the cells in the medium (in particular their fall velocity in the medium in the absence of agitation, that is in static conditions, or the fall velocity of the substrates to which the cells are anchored, and the shear stress ($\tau$) connected with it are described by the following equations:

$$V_{rel} = \frac{[2gr^2(\rho_\rho - \rho_f)]}{9\mu}; \quad (1) \text{ and } (2)$$

$$\tau = \frac{3\mu V_{rel}}{2r},$$

where g is acceleration due to gravity, r the radius of the cell substrates, $\rho_\rho$ the density of the substrates, $\rho_f$ the density of the culture medium and $\mu$ the viscosity of the medium. It is therefore clear from equations (1) and (2) that corresponding to a reduction in the relative velocity there is a reduction in shear stress.

A method for minimising the relative velocity is to make the density of the medium as close as possible to that of the cell substrates, which can be achieved by the addition to the medium of one of the substances listed above. As stated earlier, it is also necessary to compensate for sedimentation. By means of the spiral flow obtained in the spiral capillary device 12, the weight force is averaged to a low value because of the hydrodynamic thrust and in this way the cell substrates are made to rotate, so that the cells attached to them are subjected on average to a condition of reduced gravity.

On the other hand it is known that agitation may produce eddies, the smallest of which (Kolmogoroff eddy) causes localized shear stress on the cell substrates in the bioreactor 1 (or on the cells themselves where there are no substrates). Damage to the cells because of this shear stress is however generally encountered only when the size of the eddy is smaller than that of the cell substrates. Therefore by a suitable choice of substrate size and by introducing a substantially laminar flow in the reservoir 7 (which can be obtained both by careful control of the velocity of the medium and by the absence of mechanical agitation in the reservoir 7), the diameter of the Kolmogoroff eddies is greater than the diameter of the cell substrates. This and the low pressure used so as not to destroy the structure of the eddies present in any case ensure low surface shear stress. In addition, the eddies which envelop, trap and transport the cell substrates produce very low shear stress without any damage to the cells themselves.

Moreover, it can be demonstrated that the shear stress caused by the Kolmogoroff eddies can be described quantitatively by the following formula:

$$\tau_{max}=5.33\rho(\epsilon\upsilon)^{1/2} \quad (3)$$

where $\rho$ is the density of the medium, $\epsilon$ the empirical rate of energy dissipated by turbulence averaged over the volume, $\upsilon$ the kinematic velocity of the medium equal to $\mu/\rho$ $e^{(\epsilon\upsilon)^{1/2}}=v^2$ that is the velocity of flow of the medium.

The characteristics and growth of the cells on substrates and immersed in the medium inside the bioreactor 1 are studied using non-destructive techniques, such as NMR spectroscopy, for example. For this purpose, the container 7 is inserted into an NMR spectrometer to study the cell metabolism on-line, by obtaining the appropriate NMR spectrums. For spectroscopic analysis, various nuclei and the most varied pulse sequences can be used in order to identify cell damage, structures, forms, flows and the location of intracellular or extracellular metabolites and the intracellular or extracellular pH.

The cell count, analysis and collection of data are carried out by means of appropriate dedicated software.

From an analysis of the experiments completed, it is clear that in the bioreactor 1, the cells are subject to simulated microgravity. In particular, it has already been shown in the literature that cell cultures in reduced gravity disorganize their cytoskeletons. This disorganization has been observed in the bioreactor according to the invention, and is moreover compatible with the observations made in the experiments carried out in other bioreactors of the Rotating Wall Vessel (RWV) type.

EXAMPLES

The Bioreactor

The bioreactor used in these examples consists of a 20 mm tube for NMR (Wilmad) in an NMR spectrometer of the type Bruker AMX 500 WB. The plug of this tube was modified to take the first capillary line 6, for inward flow of the medium into the tube and the two outlet lines 9, 10: all the lines are produced from 0.2 mm diameter Teflon.

All the lines are connected to the reservoir 2 using PharMed® Tubing in order to avoid oxygen losses. The temperature is also kept constant both in the perfusion system and in the NMR spectrometer.

Where adherent cells are used, these are made to grow on microcarrier beads (for example Cytodex 3) for 48 hours until a number of approximately $2$-$10 \times 10^6$ is reached, and are inserted into the NMR tube. Moreover, the medium is modified so as to increase its density (up to $\rho=1.0195$ g/ml by the addition of 13% of D2O deuterated water ($\rho=1.11$ g/ml)) and HEPES is also added in a quantity such as to obtain a pH which is constant and equal to 7.4. It has been observed that the addition of deuterated water in this concentration does not alter growth.

From equations (1) and (2) it can be seen that the addition of D2O gave a reduction in relative velocity of 40%, since the density of the medium was altered, bringing it closer to that of the beads, and consequently a similar reduction in shear stress. The value of the shear stress in this case, calculated from the formulae cited, was equal to 0.07 dyne/cm2, an extremely low value compared with that obtainable in known bioreactors, of the order of unity.

Considering that in this specific case, the velocity is equal to $v=2.7*10^{-2}$ cm/s (or 4 cm in 144 seconds), it is found that $\upsilon=7.5*10^{-3}$ cm$^2$/s; from equation (3) it is found that the maximum shear stress assumes a value of $\tau_{max}=3.9*10^{-3}$ dyne/cm2. Under these conditions, the Kolmogoroff eddies are characterized by the following length:

$$\eta=(\upsilon^3/\epsilon)^{1/4}=(4.21*10^{-7}/7*10^{-5})^{1/4}=0.28_{cm}$$

which is greater than the diameter of the beads.

As soon as the cells are placed inside the bioreactor, perfusion of the medium is started at a rate of 3 ml/min at a controlled temperature and oxygenation (the oxygenation is such that the CO2/O2 ratio is 5/95).

Oxygen is supplied inside the reservoir 2 at a rate of 250 ml/min. The rate of perfusion of the medium is kept constant by means of peristaltic pumps by Masterflex, General Control, Italy.

This example of a bioreactor is not intended to limit the scope of the present invention, in particular the dimensions of the bioreactor and of the inlet and outlet lines may be varied by a person skilled in the art, taking care to comply with the overall fluid dynamics behaviour.

Example 1

Culture of Endothelial Cells

As an explanatory example, endothelial cells were chosen (in particular, human umbilical vein endothelial cells (HUVC) because of their particular sensitivity to various stresses (shear stress, gravity, different oxygenation)).

Culture Conditions

Cells of the HUVEC-C s type were obtained from the American Type Culture Collection (ATCC) and were cultured in flasks containing gelatine with M199 medium containing 10% of foetal calf serum, ECGF (150 µg/ml) and heparin (5 U/ml).

The cells were seeded on beads of the Citodex 3 type, with a density of 1.04 g/cm3 and a size of 175/210 µm.

At appropriate times, the cells were treated with tripsin, coloured with trypan blue and counted with a Burker camera. The changes in the cytoskeleton were observed by immunofluorescence.

31P NMR spectrums were obtained in Fourier transform at 202.46 MHz using a Bruker AMX 500 WB spectrometer at a temperature of 37° C. with the 20 µsec pulses at 60° C. with an interval of 2 seconds. For the presence of D2O, the resolution was obtained in the usual manner (Bradamante et al. Biochem. Biophys Res Commun. 196:872-878, (1993); Bradamante et al. Biochim Biophys Acta 1243:1-8 (1995)).

Figure 3:
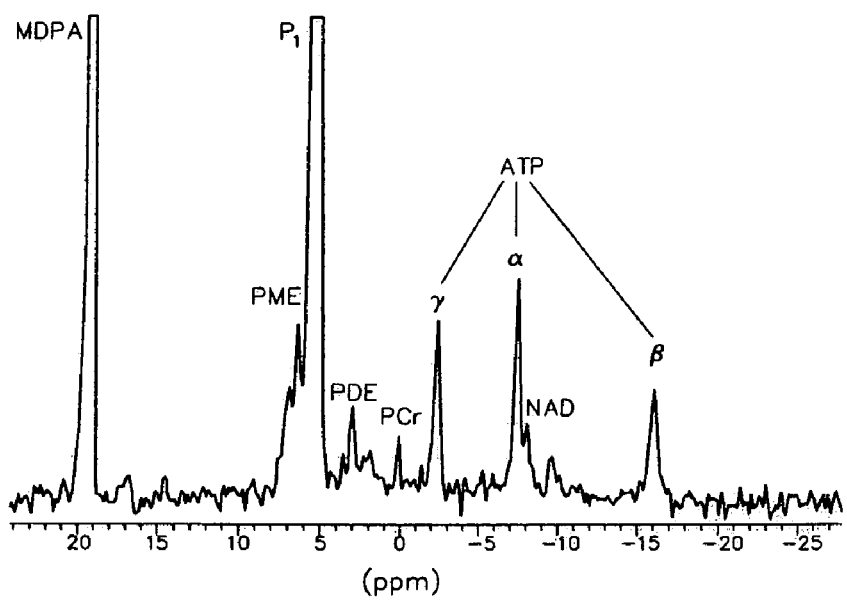
FIG. 3 is an NMR spectrum of a cell culture obtained by means of the bioreactor in FIG. 1.

FIG. 3 shows a 31P NMR spectrum obtained with 10200 accumulations of the HUVEC cells grown on the beads described above in the bioreactor 1. The NMR spectrum shows the resonances of the phosphates at high energy (α-, β-, γ-nucleotide triphosphate, phosphocreatine (PCr)) and inorganic phosphate (Pi), phosphomonoesters, phosphodiesters and NAD. Since a significant reduction in PCr was observed in conditions of poor oxygenation (Loike et al. Op. cit.), the fact that PCr is visible guarantees that oxygenation is adequate. The data obtained were compared with those observed in experiments using the RWV systems on the same type of HUVEC cells. In particular, the experiments reported by some authors were taken as controls (Muhitch et al. Cytotechnology 32:253-263 (2000); Chopra et al. In Vitro Cell Dev Biol 33 :432-442 (1997); Carlsson et al. J. Gravit Physiol 9: 272-273 (2002); Saarinen et al. Biotechnol Prog. 19: 1335-1341 (2003)), experiments which were substantially reproduced, comparable results being obtained. The data obtained confirm that the conditions obtained by means of the bioreactor 1 are similar to or better than those obtained using the RWV system (not compatible with NMR spectroscopy).

Figure 4:
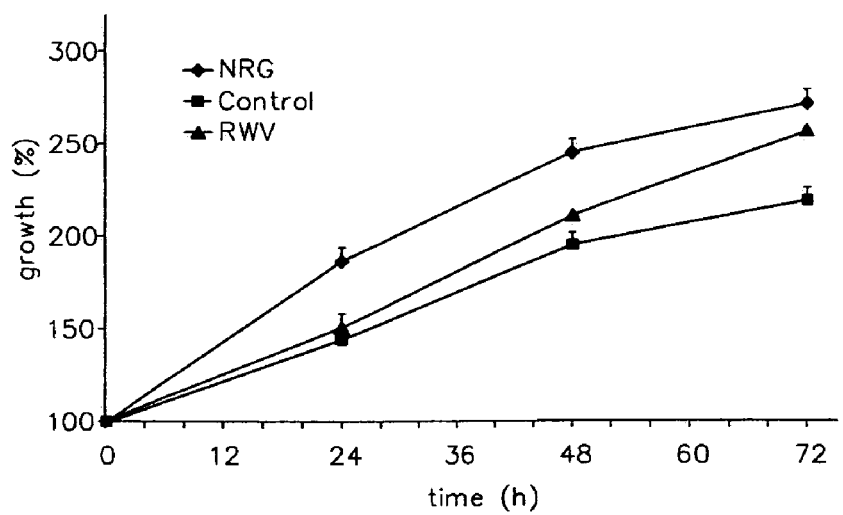
FIG. 4 is the graph of a curve representing cell growth as a function of time of cells cultured inside the bioreactor in FIG. 1 compared with cell growth of the same cells cultured according to the known technology.

FIG. 4 shows the data obtained in the experiment described relating to the percentage growth of the HUVEC cells as a function of time in the bioreactor according to the invention. The same graph gives growth values for the same cells in an RWV device together with the data obtained for HUVEC cell growth in static conditions.

The effect of microgravity was confirmed by analyzing the disorganization of the cytoskeleton of the endothelial cells (Carlsson et al., article cited). The total duration of the experiment, inside the NMR spectrometer, was 72 h.

Example 2

Production of Glutathione (GSH) from Yeast Cells

Glutathione is a known tripeptide (N-(N-L-gamma-glutamyl-cysteinyl)glycin) with cell localization, used mainly as an antioxidant and in the detoxification of xenobiotics, carcinogens (Wu et al. J. Nutr. 134:489-492 (2004)) and free radicals. Recently, it has been demonstrated that GSH is involved in the mechanisms of intracellular and extracellular signalling (Carelli et al. Science 277: 1681-1684, (1997)). It is used in the food sector as a biological antioxidant.

GSH is produced industrially by fermentation and extracted from microbial cells. To improve the yield, some production methods disclosed for example in patents U.S. Pat. Nos. 4,596,775, 4,582,801, FR2692280, and US2004048337 make use of mutated strains.

The optimizing of production is reported by various authors: the yields reported are respectively 17 mg/g dry biomass (Udeh, K. O.; Achremowicz, B. Acta Microbiologica Polonica 46: 105-114 (1997)) and 124.93 mg/l (Liu, C-H.; Hwang, C-F.; Liao, C-C. Process Biochemistry 34, 1.7-23 (1999)).

To solve the problems connected with low specific productivity and difficulties in extraction, a recent proposal has been to use detergents to promote permeability and therefore the extracellular accumulation of GSH (Wei, G.; Li, Y.; Du, G.; Chen, J. Process Biochemistry 38:1133-1138 (2003)). The use of detergents does however create problems with cell growth.

In the light of this information, production of a biomass with high specific productivity for GSH is still a long way from industry objectives.

Culture Conditions

Cells of the yeast *Saccharomyces Cerevisiae* (of the type normally available commercially) are cultured directly in the bioreactor in an activation medium having the following composition per 100 ml of water: KH2PO4 0.35 g, KOH 0.037 g, (NH4)2SO4 0.7 g, MgSO4 0.05 g, Na3 citrate 1 g, glucose 4 g, cysteine 0.4 g, glycin 0.4 g.

Yeast cells in a concentration equal to 2.5% of dry weight are suspended directly in the activation medium.

At suitable intervals (24 hours), the cells are separated from the supernatant activation medium, permeablised and the concentration of intracellular glutathione (GSH) produced is measured by analysis using high-performance liquid chromatography (HPLC); analysis by high-performance liquid chromatography (HPLC) of the supernatant activation medium provides a measurement of the extracellular GSH.

In the case considered, the GSH produced is primarily extracellular, that is directly produced using the bioreactor in the culture medium, while the intracellular GSH remains within the range of values 1-1.4%.

The data obtained were compared with those present in US patent 2004048337. A comparison between the results is given in the following table.

Production of intracellular and extracellular glutathione from *Saccharomyces cerevisiae*

| Time (h) | US2004048337 Biomass (g/l) | NRG Biomass (g/l) | US2004048337 GSH (%) total | NRG GSH (%) extracellular |
|---|---|---|---|---|
| 0 | 0.5 | 0.25 | 1.4 | 0.2 |
| 24 | 0.5 | 0.32 | 3.7 | 7 |

From the data in the table, it is clear that the yeast cells cultured in the bioreactor disclosed by the invention give rise to a very much higher production of extracellular GSH than that obtained with known techniques. The invention therefore solves the problem addressed, securing numerous advantages compared with the known reference technology.

A first advantage consists in the fact that the bioreactor according to the invention is particularly versatile and can be used with the most varied types of cell cultures and investigation devices, in particular proving highly suitable for NMR spectroscopy.

From a comparison of the data obtained on cell vitality and proliferation in the bioreactor according to the invention, there are indications of accelerated proliferation compared with conventional bioreactors.

Moreover, the bioreactor is produced in such a way that the medium is resident inside the container for a short time, to ensure optimum conditions for the culture cells. In fact, considering the volume of the container 7 equal to 18 ml and the volumetric flow of the circulation pump fixed at 3 ml/min, the time for which the medium stays in contact with the substrates (beads) is found to be approximately 360 seconds. Furthermore, the fact that oxygenation occurs inside the reservoir containing the medium means that the cells are not in direct contact with the bubbles of the gas.

Packing of the beads is prevented by controlling the density of the medium and by the velocity of the latter, that is without using agitation, whether mechanical or produced by gas.

Moreover, low shear stress is obtained by reason of the fluid dynamic conditions produced by the spiral capillary placed inside the container.

Finally, the cells cultured in the bioreactor disclosed by the invention give rise to increased production of metabolites.

The invention claimed is:

1. A bioreactor comprising a container capable of containing a cell culture, a first inlet line for the inward flow of a culture medium to the inside of said container and a second outlet line for the outward flow of the culture medium from said container, characterized in that said first inlet line is connected to a spiral-shaped capillary tube, said spiral-shaped capillary tube having a form such that when said medium is made to flow inside said first line and made to flow out from said second line, hydrostatic thrust and hydrodynamic forces produce a condition of simulated reduced gravity with respect to said cells, inside said container.

2. A bioreactor according to claim 1, in which said spiral-shaped capillary tube is positioned close to the bottom of said container.

3. A bioreactor according to claim 1, in which said container is a tube for NMR spectroscopy.

4. A bioreactor according claim 1, comprising a reservoir into which said medium is introduced, said first line running from said reservoir and said second line extending to said reservoir.

5. A bioreactor according claim 1, comprising means for circulating said medium, capable of causing said medium to circulate from and to said container.

6. A bioreactor according to claim 4, comprising delivery means for the introduction of oxygen into said medium inside said reservoir.

7. A bioreactor according to claim 4, comprising means for sensing the pH of said medium positioned inside said reservoir.

8. A bioreactor according to claim 4, comprising means for maintaining a constant temperature of said medium inside said reservoir.

9. A bioreactor according to claim 1, comprising a third line for outward flow of the medium from said container.

* * * * *